(12) United States Patent
Ume et al.

(10) Patent No.: US 8,146,429 B2
(45) Date of Patent: Apr. 3, 2012

(54) METHODS AND SYSTEMS FOR CLASSIFYING THE TYPE AND SEVERITY OF DEFECTS IN WELDS

(75) Inventors: Ifeanyi Charles Ume, Atlanta, GA (US);
Renfu Li, Johnes Creek, GA (US);
Matthew Rogge, Atlanta, GA (US);
Tsun-Yen Wu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 412 days.

(21) Appl. No.: 12/534,581

(22) Filed: Aug. 3, 2009

(65) Prior Publication Data
US 2011/0023610 A1 Feb. 3, 2011

(51) Int. Cl.
*G01N 29/04* (2006.01)
(52) U.S. Cl. .......... 73/622; 73/599; 73/600; 73/602
(58) Field of Classification Search .......... 73/622, 73/597, 598, 599, 600, 602, 618, 627
See application file for complete search history.

(56) References Cited

U.S. PATENT DOCUMENTS

| | | | |
|---|---|---|---|
| 3,436,958 A * | 4/1969 | Proctor | 73/600 |
| 3,575,044 A | 4/1971 | Gibbs et al. | |
| 3,585,851 A * | 6/1971 | Walther | 73/624 |
| 3,693,158 A | 9/1972 | Uthe | |
| 3,791,199 A | 2/1974 | Toth et al. | |
| 4,298,808 A | 11/1981 | Hill | |
| 4,522,064 A * | 6/1985 | McMillan | 73/592 |
| 4,531,409 A | 7/1985 | Koch et al. | |
| 4,869,109 A | 9/1989 | Miglianico et al. | |
| 5,283,418 A | 2/1994 | Bellows et al. | |
| 5,475,613 A * | 12/1995 | Itoga et al. | 702/39 |
| 5,476,010 A | 12/1995 | Fleming et al. | |
| 5,544,256 A | 8/1996 | Brecher et al. | |
| 5,619,998 A | 4/1997 | Abdel-Malek et al. | |
| 5,674,415 A | 10/1997 | Leong et al. | |
| 5,724,138 A | 3/1998 | Reich et al. | |
| 5,764,859 A | 6/1998 | Kim et al. | |
| 5,907,100 A | 5/1999 | Cook | |

(Continued)

OTHER PUBLICATIONS

Amara Graps An Introduction to Wavelets IEEE Computational Science and Engineering, Summer 1995, vol. 2, No. 2., Published by IEEE Computer Society, 10662 Los Vaqueros Circle, Los Alamitos, CA 90720, USA.

(Continued)

*Primary Examiner* — J M Saint Surin
(74) *Attorney, Agent, or Firm* — Dinsmore & Shohl LLP

(57) ABSTRACT

A method for determining the type of a defect in a weld may include determining a defect location and a corresponding defect signal by analyzing ultrasonic response signals collected from a plurality of measurement locations along the weld. The defect signal and the plurality of defect proximity signals corresponding to ultrasonic response signals from measurement locations on each side of the defect location may then be input into a trained artificial neural network. The trained artificial neural network may be operable to identify the type of the defect located at the defect location based on the defect signal and the plurality of defect proximity signals and output the type of the defect located at the defect location. The trained artificial neural network may also be operable to determine a defect severity classification based on the defect signal and the plurality of defect proximity signals and output the severity classification.

20 Claims, 10 Drawing Sheets

U.S. PATENT DOCUMENTS

| | | | |
|---|---|---|---|
| 5,932,123 | A | 8/1999 | Marhofer et al. |
| 6,125,705 | A | 10/2000 | Johnson |
| 6,335,504 | B1 | 1/2002 | Ling et al. |
| 6,484,584 | B2 * | 11/2002 | Johnson et al. ............... 73/624 |
| 6,497,150 | B1 | 12/2002 | Kruzic |
| 6,532,820 | B1 | 3/2003 | Fleming et al. |
| 6,532,821 | B2 | 3/2003 | Lamouche et al. |
| 6,597,997 | B2 | 7/2003 | Tingley |
| 6,640,632 | B1 | 11/2003 | Hatanaka et al. |
| 6,848,312 | B2 | 2/2005 | Georgeson |
| 6,857,553 | B1 | 2/2005 | Hartman et al. |
| 6,896,171 | B2 | 5/2005 | Den Boer et al. |
| 6,923,067 | B2 * | 8/2005 | Coen et al. ............... 73/627 |
| 6,937,329 | B2 | 8/2005 | Esmiller |
| 6,948,369 | B2 | 9/2005 | Fleming et al. |
| 7,094,989 | B2 | 8/2006 | McJunkin et al. |
| 7,132,617 | B2 | 11/2006 | Lee et al. |
| 7,204,147 | B2 | 4/2007 | Fujimoto et al. |
| 7,234,355 | B2 | 6/2007 | Dewangan et al. |
| 7,516,022 | B2 | 4/2009 | Lee et al. |
| 7,557,558 | B2 | 7/2009 | Barrow |
| 7,728,254 | B2 | 6/2010 | D'Angelo et al. |
| 7,784,347 | B2 * | 8/2010 | Messer et al. ............... 73/618 |
| 7,851,753 | B2 * | 12/2010 | Uto et al. ............... 250/310 |
| 7,926,349 | B2 * | 4/2011 | Sargent ............... 73/588 |
| 2002/0017139 | A1 | 2/2002 | Kluft et al. |
| 2003/0167616 | A1 | 9/2003 | Harding et al. |
| 2003/0200809 | A1 | 10/2003 | Hatanaka et al. |
| 2005/0230360 | A1 | 10/2005 | Maev et al. |
| 2007/0038400 | A1 | 2/2007 | Lee et al. |
| 2007/0234809 | A1 | 10/2007 | Klein et al. |
| 2008/0072674 | A1 | 3/2008 | Ume et al. |
| 2008/0210010 | A1 | 9/2008 | Orth et al. |

OTHER PUBLICATIONS

Christopher Torrence, Gilbert P. Compo A Practical Guide to Wavelet Analysis Program in Atmospheric and Oceanic Sciences, University of Colorado, Boulder, Colorado Bulletin of the American Meteorological Society, vol. 79, No. 1, Jan. 1998.

Neural Networks, [Retrieved Aug. 3, 2009] Retrieved from the internet <url:http://learnartificalneuralnetworks.com>.

Back propagation Neural Network, [Retrieved Aug. 3, 2009] Retrieved from the internet <url:http://learnartificialneuralnetworks.com/backpropagation.htm>.

P.K. Simpson Foundations of Neural Networks Proceedings of the Adaptive Control Systems Technology Symposium, Oct. 24-25, 1994, pp. 16-37.

Office Action mailed Oct. 27, 2011 as it relates to U.S. Appl. No. 12/488,396.

Office Action mailed Jan. 11, 2012 as it relates to U.S. Appl. No. 12/534,296.

* cited by examiner

METHODS AND SYSTEMS FOR CLASSIFYING THE TYPE AND SEVERITY OF DEFECTS IN WELDS

CROSS REFERENCE TO RELATED APPLICATIONS

This specification is related to commonly assigned U.S. patent application Ser. No. 12/534,296 filed Aug. 3, 2009 entitled "METHODS AND SYSTEMS FOR DETECTING DEFECTS IN WELDED STRUCTURES UTILIZING PATTERN MATCHING" and U.S. patent application Ser. No. 12/488,396 filed Jun. 19, 2009 entitled "METHODS AND SYSTEMS FOR DETECTING DEFECTS IN WELDED STRUCTURES".

TECHNICAL FIELD

The present specification generally relates to methods and systems for detecting and classifying defects in welded structures and, more specifically, to methods and systems for identifying the type and severity of defects in welded structures utilizing ultrasonic inspection in conjunction with an artificial neural network.

BACKGROUND

Various welding techniques are commonly utilized to join metallic parts to produce a wide variety of articles of manufacture such as, for example, automobile components, aircraft components, heavy equipment and machinery. The quality of the weld may play an important role in the structural integrity of the welded structure in which it is employed. However, during the welding or joining operation, defects may be introduced or formed in the weld. Such defects may include blowholes, voids, porosity and insufficient weld penetration depth. Each of these defects may decrease the load bearing capacity of the welded structure. For example, some types of defects may act as stress risers or stress concentrators which may impact the static, dynamic and fatigue strength of the weld and the welded structure. Therefore, it is important to accurately detect and locate potential defects in the welds.

When welds are formed automatically, such as by an automated or robotic welding system, the quality of a weld may be assessed by destructively testing a random sampling of the welded structures that are produced. Destructive tests, such as cut-checks, may be time-consuming and may generate excess product waste. Moreover, automation of such destructive testing methodologies may not be possible.

Efforts have been made to develop various non-destructive testing techniques for detecting defects in welds. However, most of these techniques may not be easily incorporated into manufacturing environments. Moreover, such non-destructive techniques may be unable to identify the specific types of defects present in the weld and characterize the severity of the defects.

Accordingly, a need exists for alternative methods and systems for detecting defects in welds and determining the type and severity of the detected defects.

SUMMARY

In one embodiment, a method for determining the type of a defect in a weld may include determining a defect location and a corresponding defect signal by analyzing ultrasonic response signals collected from a plurality of measurement locations along the weld. The defect signal and a plurality of defect proximity signals corresponding to ultrasonic response signals from measurement locations on each side of the defect location may then be input into a trained artificial neural network. The trained artificial neural network may be operable to identify the type of the defect located at the defect location based on the defect signal and the plurality of defect proximity signals and output the type of the defect located at the defect location.

In another embodiment, a method for determining a severity of a defect in a weld may include determining a defect location and a corresponding defect signal by analyzing ultrasonic response signals from a plurality of measurement locations along the weld. The defect signal and a plurality of defect proximity signals corresponding to ultrasonic response signals from measurement locations on each side of the defect location may then be input into a trained artificial neural network. The trained artificial neural network may be operable to determine a defect severity classification of the defect located at the defect location based on the defect signal and the plurality of defect proximity signals and output the defect severity classification of the defect located at the defect location.

In yet another embodiment, a defect classification system may include a controller, an acoustic signal generator, an acoustic signal detector, and a positioning device. The acoustic signal generator, the acoustic signal detector and the positioning device may be electrically coupled to the controller. The controller may be programmed to: induce ultrasonic signals at multiple measurement locations along the weld with the acoustic signal generator; collect an ultrasonic response signal from each of the measurement locations with the acoustic signal detector and store each ultrasonic response signal in a memory operatively associated with the controller; determine a defect location and a defect signal by analyzing the ultrasonic response signal from each of the measurement locations; determine a plurality of defect proximity signals, wherein the defect proximity signals correspond to ultrasonic response signals from measurement locations on each side of the defect location; input the defect signal and the plurality of defect proximity signals into a trained artificial neural network operatively associated with the controller, wherein the artificial neural network is operable to identify the type of the defect located at the defect location based on the defect signal and the plurality of defect proximity signals; and output the type of the defect located at the defect location.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
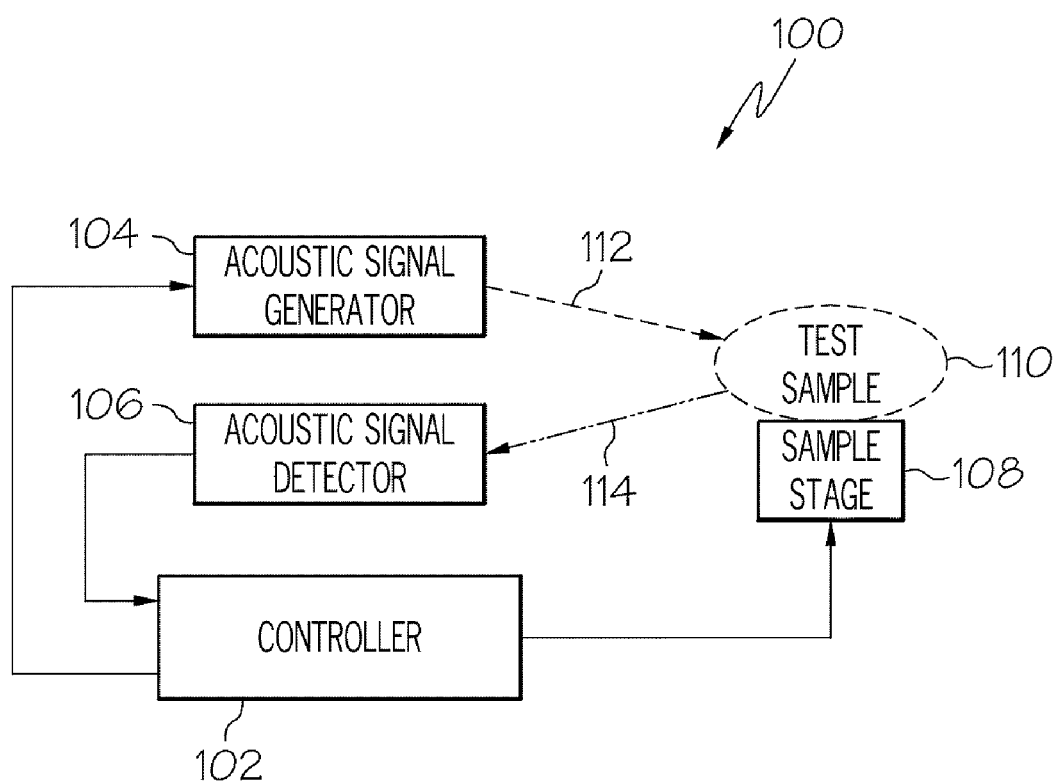
FIG. 1 is a block diagram of a defect classification system according to one or more embodiments shown and described herein.

FIG. 1 generally depicts one embodiment of a defect classification system for determining the type and/or severity presence and location of defects in a weld. The system may generally comprise an acoustic signal generator and an acoustic signal detector coupled to a controller. The various components of the defect classification system and methods of using the defect classification system to determine the type and/or severity of defects in a welded structure will be described in more detail herein.

Referring now to FIG. 1, a block diagram of a defect classification system 100 is depicted. The defect classification system 100 may generally comprise an acoustic signal generator 104, an acoustic signal detector 106 and a sample stage 108, each of which are electrically coupled to a controller 102. Accordingly, it should be understood that the solid lines and arrows shown in FIG. 1 are generally indicative of the electrical interconnectivity of the various components of the defect classification system 100. It should also be understood that the solid lines and arrows are indicative of electronic signals, such as control signals and/or data signals, propagated between the various components of the defect classification system 100. Further, it should be understood that the dashed line and arrow between the acoustic signal generator 104 and the test sample 110 is indicative of excitation signals 112 transmitted from the acoustic signal generator 104 to a test sample 110 while the dashed line and arrow between the test sample 110 and the acoustic signal detector 106 is indicative of an ultrasonic response signal 114 emitted from the test sample 110 due to the received excitation signal 112 from the acoustic signal generator 104.

In the embodiments shown and described herein the acoustic signal generator 104 may be a device operable to excite an ultrasonic signal in the test sample 110 without physically contacting the test sample. In one embodiment, the acoustic signal generator 104 may comprise a pulsed laser source operable to excite an ultrasonic signal in the test sample 110 by directing a series of laser pulses onto the surface of the test sample. In another embodiment, the acoustic signal generator 104 may comprise an electromagnetic acoustic transducer (EMAT) operable to excite an ultrasonic signal in the test sample 110 using electromagnetic fields. It should be understood that the acoustic signal generator 104 may comprise other devices suitable for generating ultrasonic signals in the test sample 110.

The acoustic signal detector 106 may generally be a device operable to sense or detect the ultrasonic response signals 114 generated in the test sample 110 without physically contacting the test sample. Accordingly, in one embodiment, the acoustic signal detector 106 may comprise an EMAT sensor operable to detect the acoustic response signal generated in the test sample 110. However, it should be understood that various other non-contact transducers and/or acoustic sensors may be used to detect the ultrasonic response signal 114.

In one embodiment (not shown), where the acoustic signal generator is an EMAT, the EMAT may be used to both excite an ultrasonic signal in the test sample and to detect the ultrasonic response signal from the test sample. Accordingly, it should be understood that a single EMAT may be used as both the acoustic signal generator and the acoustic signal detector.

In the embodiment of the defect classification system 100 shown in FIG. 1, the sample stage 108 may comprise a fixture (not shown) for mounting a test sample to the sample stage. The sample stage 108 may comprise one or more actuators (not shown), such as motors and/or stepper motors, mechanically coupled to the stage and electrically coupled to the controller 102. The controller 102, in conjunction with the actuators, may be operable to adjust the position of sample stage 108 and test sample 110 relative to the acoustic signal generator 104 and acoustic signal detector 106 such that the excitation signals 112 emitted by the signal generator may be scanned over the test sample 110 in a controlled manner.

While the embodiments shown and described herein depict the test sample as being fixtured to a moveable sample stage, it should be understood that, in other embodiments (not shown), the acoustic signal generator and the acoustic signal detector may be attached to a moveable stage or similar positioning device electrically coupled to the controller such that the acoustic signal generator and the acoustic signal detector may be adjustably positioned relative to the test sample. Accordingly, it should be understood that the defect classification system may include at least one positioning device for adjusting the relative orientation between the test sample and the acoustic signal generator and acoustic signal detector.

The controller 102 may comprise a computer operable to execute a programmed instruction set and transmit control signals to each of the components of the defect classification system 100. The controller 102 may also be operable to store data received from the acoustic signal detector 106 and analyze the stored data to determine the presence of defects in a weld and to identify the type and severity of defects present in the weld. For example, in one embodiment, the controller 102 may be programmed with an artificial neural network (ANN) which may be trained to determine the type and severity of a defect present in the weld after the location of a defect has been determined with the controller, as will be described in more detail herein. Accordingly, it should be understood that the controller 102 may comprise or be coupled to one or more memory devices (not shown) for storing the programmed instruction set, ANN and the ultrasonic response signal data received from the acoustic signal detector. The controller 102 may also be coupled to one or more audible or visual indicators, such as a display (not shown), for providing a user with a visual or audible indication of the presence and location of defects and the type and/or severity of such defects.

Figure 2:
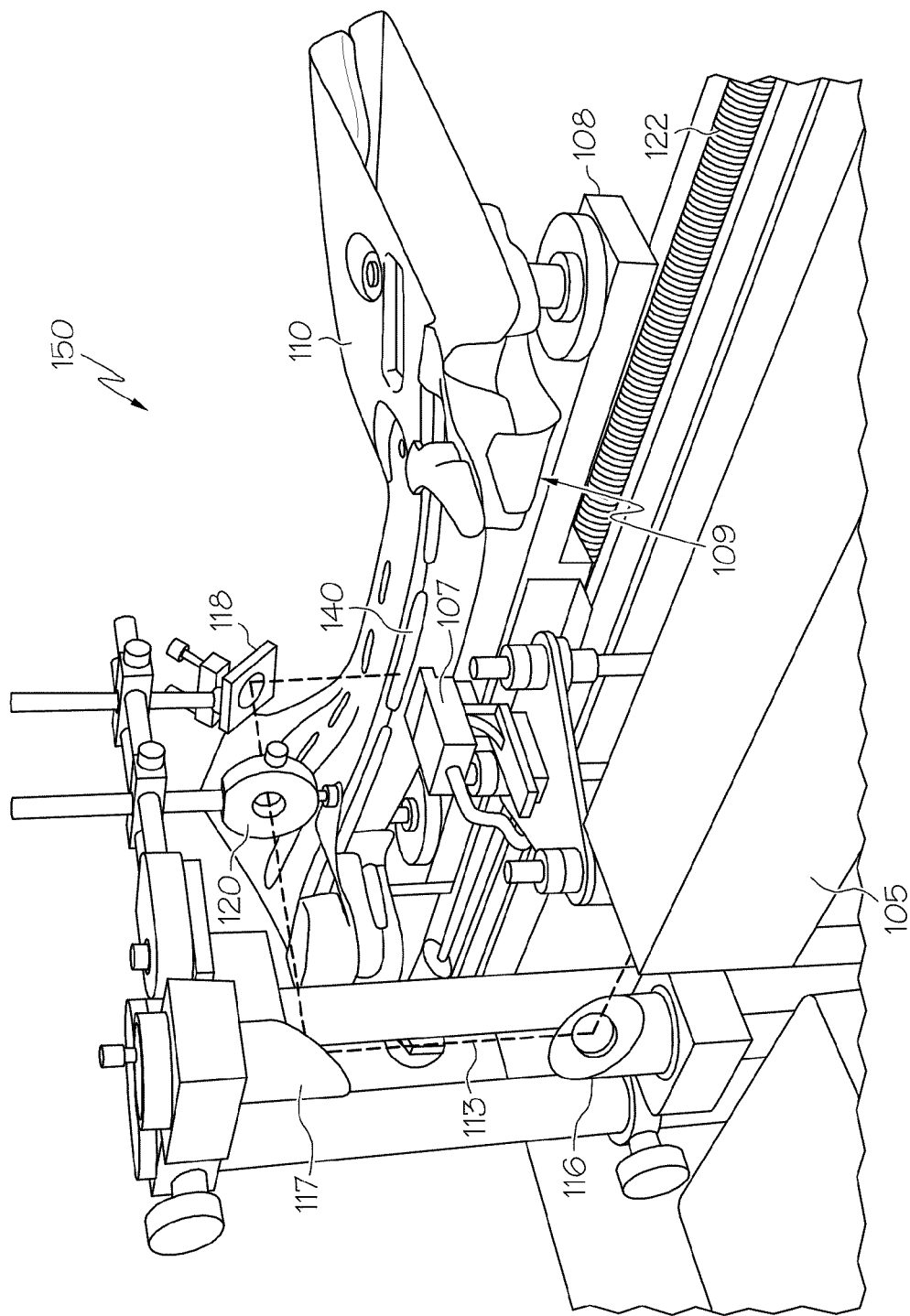
FIG. 2 depicts a defect classification system according to one or more embodiments shown and described herein.
Figure 3:
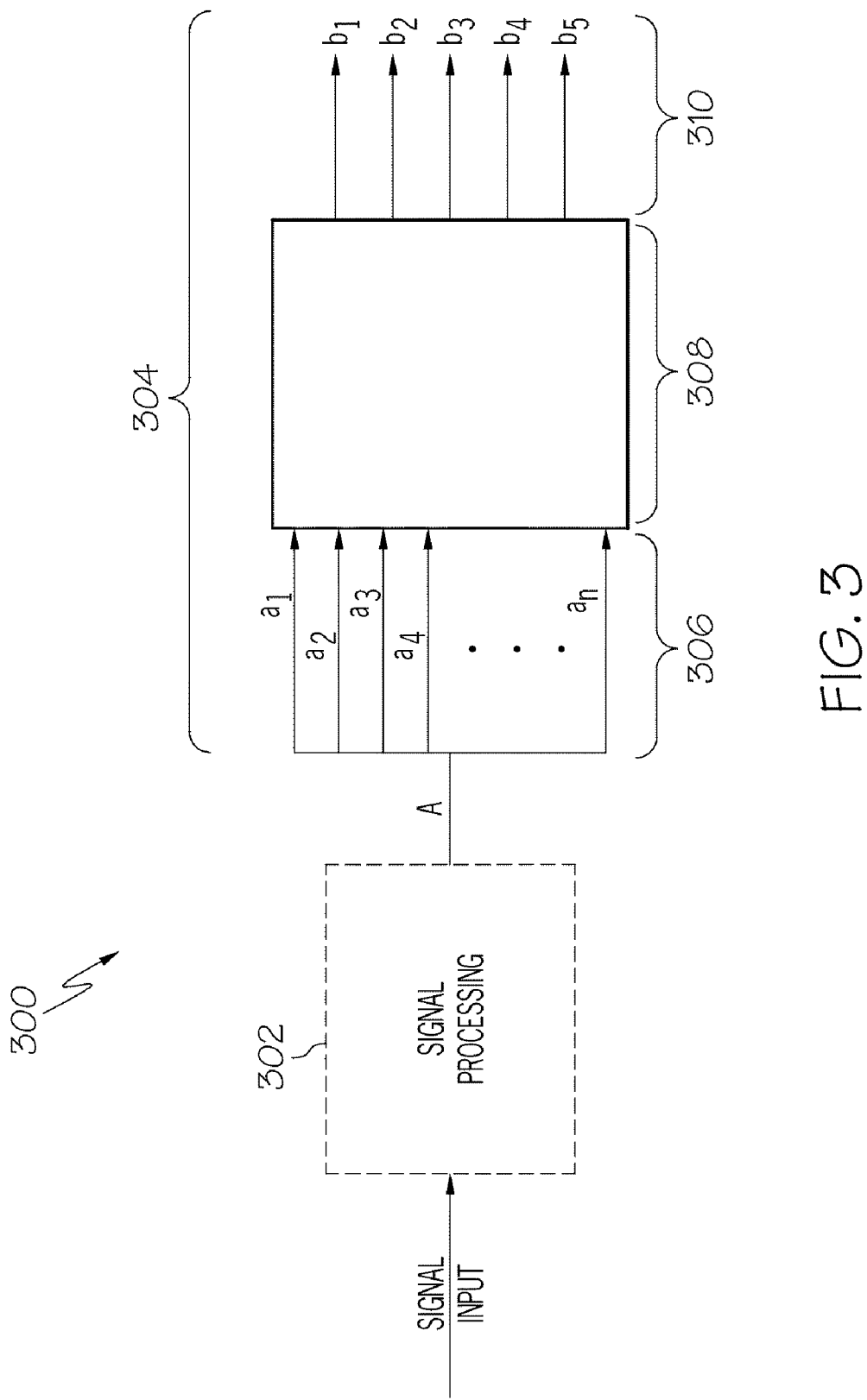
FIG. 3 depicts a block diagram of a portion of the process flow for identifying the type and/or severity of a defect according to one or more embodiments shown and described herein.
Figure 4:
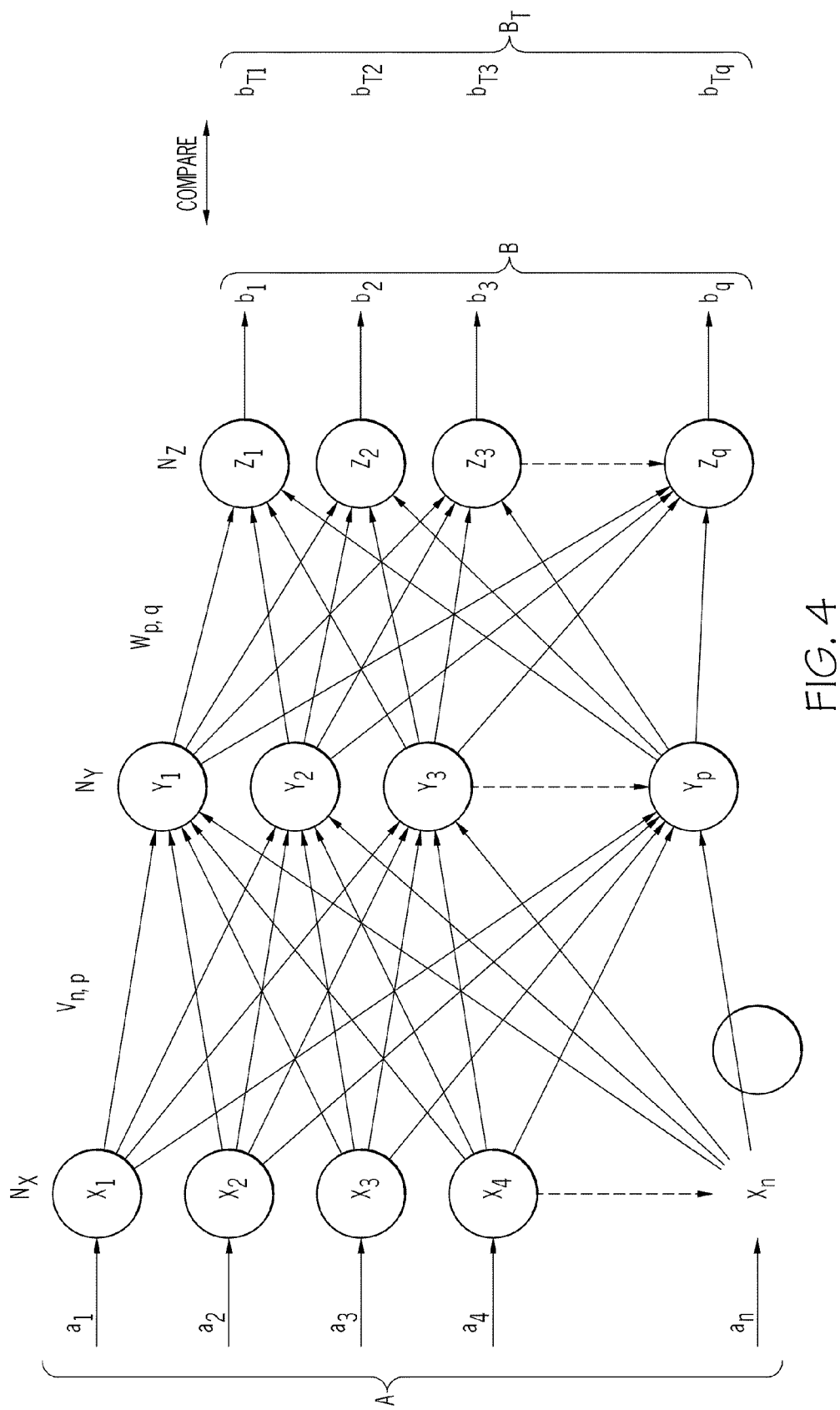
FIG. 4 schematically depicts an artificial neural network for identifying the type and/or severity of a defect according to one or more embodiments shown and described herein.

Referring now to FIGS. 2-4, one embodiment of a defect classification system 150 is illustrated. In this embodiment the acoustic signal generator is a pulsed laser source 105, such as an Inlite II-20 Nd:YAG pulsed laser manufactured by Continuum Lasers. The pulsed laser source 105 may have a 20 Hz pulse repetition rate and a pulse width of 10 ns. The spot size of the laser may be about 6 mm and each pulse may have an energy from about 55 mJ to about 450 mJ. The acoustic signal detector may be an EMAT sensor 107. In the embodiment depicted in FIG. 2 the EMAT sensor 107 is manufactured by BWXT Services, Inc. and comprises a four channel broadband receiver having a bandwidth from about 200 kHz to about 2.5 MHz. The EMAT sensor 107 may be coupled to the controller (not shown) with a data acquisition card, such as, for example, a Compuscope 8349 4 channel data acquisition card manufactured by GaGe Applied Technologies which has 14 bit resolution and a data sampling rate of 125 MHz. The sample stage 108 may include one or more fixturing device(s) 109, such as clamps, vices, etc. for holding test sample 110. The fixturing device and/or test sample may include one or more datums (not shown) such that test samples may be positioned on the sample stage with substantially the same orientation relative to the pulsed laser source 105 and the EMAT sensor 107. The sample stage 108 may be mounted to a stepper motor-driven lead screw 122 coupled to the controller such that the position of the sample stage may be adjusted with the controller.

As described hereinabove, the controller (not shown) may be programmed to determine if defects are present in the weld by analyzing ultrasonic response signals collected from the weld. Further, when a defect is determined to be present in the weld, the controller may be programmed to classify the type and/or severity of the defect. For example, after a defect is determined to be present in the weld, the controller may pass the ultrasonic response signal(s) collected from the weld to an ANN, such as the ANN 304 shown in FIG. 4, which may output a coded vector indicating the type of defect present in the weld and/or the severity of the defect in the weld. The ANN 304 may generally comprises an input layer $N_X$ (designated as 306 in FIG. 3) for receiving an input vector A of dimension n, at least one hidden layer $N_Y$ (generally designated as 308 in FIG. 3) and an output layer $N_Z$ (designated as 310 in FIG. 3) for outputting an output vector B of dimension q. The input layer $N_X$ may generally comprise a plurality of n input nodes designated as $X_1, X_2, X_3 \ldots X_n$ in FIG. 4. The number of input nodes generally corresponds to the number of components of the input vector A. The hidden layer $N_Y$ may comprise a plurality of p nodes which are designated as $Y_1, Y_2, Y_3 \ldots Y_p$ in FIG. 4. The output layer $N_Z$ may comprise a plurality of q nodes which are generally designated as $Z_1, Z_2, Z_3 \ldots Z_q$ in FIG. 4. The number of nodes q in the output layer corresponds to the desired number of components in the output vector B.

Still referring to FIGS. 2-4, the input layer $N_X$ may be coupled to the hidden layer $N_Y$ with a matrix of weights $V_{np}$ having dimensions n×p such that each node of the input layer is coupled to each node of the hidden layer $N_Y$. Similarly, the hidden layer $N_Y$ may be coupled to the output layer $N_Z$ with a matrix of weights $W_{pq}$ having dimensions p×q such that each node of the hidden layer is coupled to each node of the output layer $N_Z$. The nodes of each layer work in conjunction with the matrices of weights to map the input vector A to the output vector B thereby providing a solution to the relationship between the input vector A and the output vector B.

While the embodiment of the ANN 304 shown in FIG. 4 comprises an input layer $N_X$, an output layer $N_Z$ and single hidden layer $N_Y$, it should be understood that the ANN 304 may comprise multiple hidden layers. For example, in one embodiment, the ANN may comprise four hidden layers: a first hidden layer with 50 nodes; a second hidden layer with 35 nodes, a third hidden layer with 24 nodes, and a fourth hidden layer with 5 nodes. When the ANN comprises multiple hidden layers, as described above, additional weight matrices may interconnect the nodes of the various layers as well as the nodes of the input layer $N_X$ and the output layer $N_Z$ in a similar manner as shown in FIG. 4.

Referring to FIGS. 3 and 4, each node of each layer comprises a function, commonly referred to as an activation function, which limits the output of the node to a pre-determined range. The activation function may take on a various forms including, without limitation, linear functions, step functions, ramp functions, sigmoid functions and Gaussian functions. In the embodiments of the ANN 304 described herein, each node of each layer (i.e., the input layer, the hidden layer(s) and the output layer) has a sigmoid activation function which bounds the output of the node to a pre-determined range. The sigmoid activation function may have the form:

$$f(\gamma) = \frac{1}{1+e^{-\gamma}}$$

However, it should be understood that the sigmoid activation function may take on different forms.

Referring again to FIG. 2, in the embodiment of the defect classification system 150 shown in FIG. 2, the excitation signal used to induce ultrasonic signals in the test sample is the output beam 113 of the pulsed laser source 105 which is optically coupled to the test sample 110 with one or more mirrors. As depicted in FIG. 2, mirrors 116, 117 and 118 form an optical path between the output of the pulsed laser source 105 and the surface of the test sample 110 which directs the output beam 113 onto the surface of the test sample at the desired location. A lens 120 may be disposed in the optical path of the output beam 113 to focus the output beam. Additional optical elements (not shown) may also be inserted in the optical path such as, for example, collimators or other elements which may be used to shape the output beam 113 of the pulsed laser source 105. Further, while the embodiments of the defect classification system 150 shown in FIG. 2 depict the output beam 113 coupled to the test sample 110 with mirrors, it should be understood that the output beam may be directly coupled to the test sample without being first diverted or reflected by a mirror. In alternative embodiments (not shown), the output beam 113 of the pulsed laser source may be coupled to the test sample with one or more optical waveguides, such as an optical fiber or similar optical waveguides capable of guiding a laser beam.

As described herein, the pulsed laser source may be used to induce an ultrasonic signal in the test sample. Depending on the energy density or power of the output beam pulse incident on the surface of the test sample, the pulsed-laser source may be utilized to create an ultrasonic signal in either a thermoplastic mode of operation or an ablative mode of operation. For example, the thermoplastic mode of ultrasonic signal generation occurs when the power density of the output beam of the pulsed laser source is relatively low. The output beam rapidly heats a localized area on the surface of the test sample to a temperature less than the melting point of the material due to partial absorption of the laser radiation. The rapid increase in temperature is accompanied by a corresponding expansion of the heated material due to thermoplastic effects. The rapid expansion causes axis-symmetric tensile stresses to develop in the surface of the test sample. When the laser is switched off (e.g., between pulses), the heated region contracts. The expansion and contraction of the top surface of the test sample induces ultrasonic signals that propagate through the test sample.

Alternatively, the ablative mode of ultrasonic signal generation occurs when the power density of the output beam is high enough to heat the surface of the test sample to above the melting temperature of the material. The rapid heating creates axis-symmetric tensile stresses in the surface of the test sample, as described above. However, as the temperature on the surface of the sample exceeds the melting temperature, a small amount of material is vaporized and ejected from the surface of the test sample. Accordingly, in addition to the formation of tensile stresses, a normal reaction force is created against the surface of the sample as the material is ejected. The combination of the normal reaction force and the expansion and contraction of the top surface induces ultrasonic signals that propagate through the test sample. In general, ultrasonic signals generated through the ablative mode are generally stronger that those generated in the thermoplastic mode. In either mode of operation the ultrasonic signals induced in the test sample have frequency content from about 200 kHz to about MHz.

Figure 5:
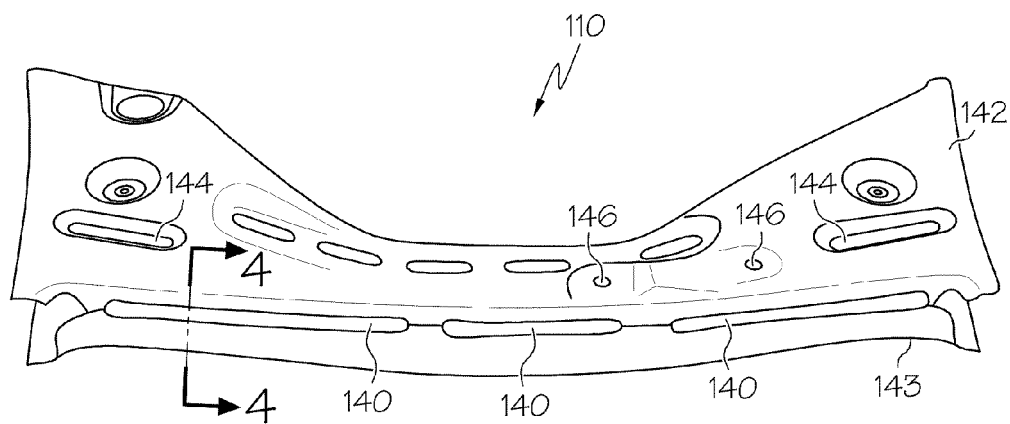
FIG. 5 depicts a test sample comprising a plurality of welds and various manufacturing features.

Referring now to FIG. 5, the test sample 110 may generally comprise a metallic structure which comprises at least one weld 140. In the embodiment of the test sample 110 shown in FIG. 4, the test sample 110 is a structural support member for an automobile which comprises an upper portion 142 and a lower portion 143, both of which are formed from thin plates of stamped sheet metal. The upper portion 142 may be joined to the lower portion 143 at a lap joint (e.g., the joint shown in FIG. 6) with welds 140. The test sample 110 may also comprise a plurality of manufacturing features including, for example, press marks 144 resulting from a stamping operation and various attachment holes 146 for connecting components to the structural support member.

Figure 6:
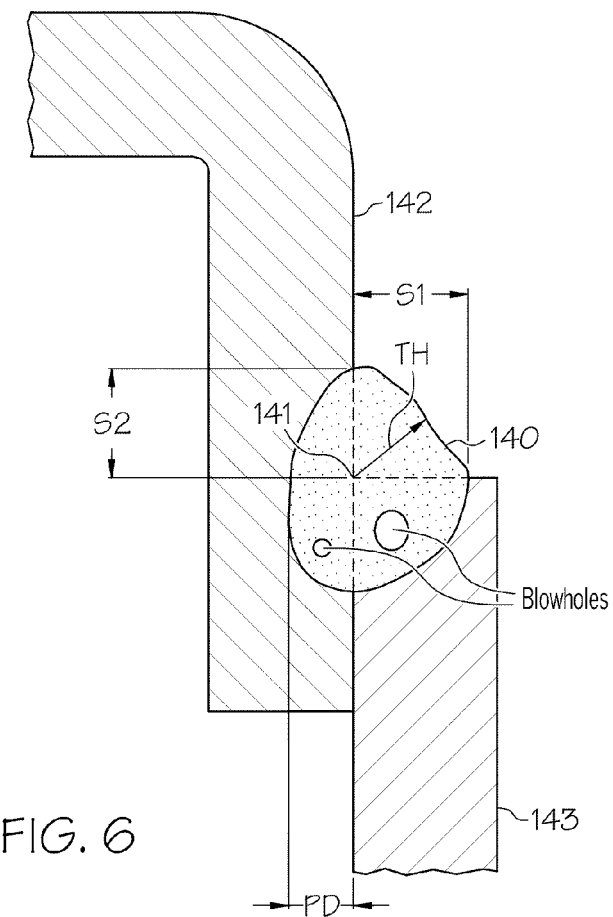
FIG. 6 depicts a cross section of a weld of the test sample of FIG. 3 illustrating various defects that may be present in the weld.

Referring now to FIG. 6 which depicts a cross section of a lap joint and weld 140 between the upper portions 142 and lower portion 143 of the test sample 110 of FIG. 5, the weld 140 may contain one or more different types of defects including, for example, blowholes, insufficient leg length (i.e., short legs), insufficient penetration depth and/or insufficient throat thickness (i.e., short throat). A blowhole defect occurs in the weld when air or gas trapped in the weld escapes from the weld as the weld is formed or as the weld cools. The escaping air or gas leaves a void in the weld and/or forms pores in the weld, each of which may decrease the strength of the weld.

The penetration depth of a weld is defined as the distance PD which the fusion portion of the weld penetrates into the base material, such as, for example, the upper portion 142 of the test sample 110. If the penetration depth is less than a specified percentage of the thickness of the base material an insufficient penetration depth or lack-of-penetration defect occurs. In the embodiments described herein, a lack-of-penetration defect occurs when the distance PD is less than about 30% of the thickness of the upper portion 142 of the test sample. However, it should be understood that the specified percentage may be greater than 30% or less than 30% depending on the application in which the test sample 110 is employed.

The legs of a lap joint weld 140 are defined as the distance between the root 141 of the weld 140 and the toe of the weld (e.g., the point where the weld intersects the base material). The legs of the weld 140 in FIG. 6 are shown as the distances S1 and S2. In the embodiments described herein, a short leg defect is present in the weld if either of the distances S1 or S2 is less than 80% of the material thickness of either the upper portion 142 or lower portion 143 of the test sample 110. However, it should be understood that the specified percentage may be greater than 80% depending on the application in which the test sample 110 is employed.

The throat thickness TH is defined as the shortest distance between the root 141 of the weld 140 and the surface of the weld, as shown in FIG. 6. A short throat defect occurs when the throat thickness of the weld 140 is less than a specified percentage of the thickness of the base material. In the embodiments shown and described herein, a short throat occurs when the throat thickness TH is less than about 70% of the thickness of either the upper portion 142 or lower portion 143 of the test sample. However, it should be understood that the specified percentage may be greater than 70% depending on the application in which the test sample 110 is employed.

Referring now to FIGS. 2, 5 and 6, ultrasonic signals induced in the thin plates which comprise the upper portion 142 and the lower portion 143 of the test sample 110 by operating the pulsed laser source in either the thermoplastic mode or ablative mode produce a series of ultrasonic Lamb waves which propagate through the test sample. The Lamb waves may be multi-modal with each mode defined by a set of frequency and wavelength pairs. Due to the different frequencies and wavelengths, each mode of the Lamb wave may react differently to different types of defects encountered in the test sample. For example, for a given type of defect, a first mode defined by a first set of frequency and wavelength pairs may be reflected by the defect while a second mode having a second set of frequency and wavelength pairs may be transmitted through the defect (i.e., the defect does not affect the second mode). Accordingly, different modes of the induced Lamb waves may be sensitive to different types of defects and, by collecting and analyzing an ultrasonic response signal from the test sample, the presence of different types of defects in the test sample may be determined, as will be described in more detail herein.

Referring now to FIG. 2, in order to determine the presence of defects in a weld on a test sample, the test sample 110 may be positioned on the sample stage 108 and attached to the sample stage 108 with one or more fixturing devices 109. The pulsed laser source 105 and EMAT sensor 107 may be positioned such that the EMAT sensor 107 collects an acoustic response signal either transmitted through the weld or reflected by the weld.

For example, in one embodiment, when an acoustic response signal transmitted through the weld is desired, the test sample 110 may be positioned such that the output beam of the pulsed-laser source is incident on one side of the weld 140 and the EMAT sensor 107 is positioned on the other side of the weld 140 and adjacent to the test sample 110, as shown in FIG. 2. Accordingly, it should be understood that the weld 140 is positioned between the point where the output beam 113 of the pulsed laser source 105 contacts the test sample 110 and the EMAT sensor 107. In this embodiment, the ultrasonic signals induced in the test sample 110 and received by the EMAT sensor 107 are transmitted through the weld 140. As defects alter the ultrasonic signal propagating through the weld the ultrasonic signal is transformed to an ultrasonic response signal which is received by the EMAT sensor 107. The ultrasonic response signal carries with it information concerning the presence of defects in the weld 140. Further, the ultrasonic response signal(s) may be correlated to a position along the length of weld 140 and test sample 110 based on the relative positioning between the test sample 110 and the point where the output beam of the pulsed laser source contacts the test sample 110 and/or the position of the EMAT sensor 107.

In another embodiment (not shown), when an acoustic response signal reflected by the weld is desired, the EMAT sensor may be positioned on one side of the weld and the output beam of the pulsed-laser source may be directed onto the test sample on the same side of the weld as the EMAT sensor. The ultrasonic response signal induced in the test sample by the pulsed-laser source propagates through the test sample to the weld which reflects at least a portion of the signal (e.g., the ultrasonic response signal), which is detected by the EMAT sensor. Because portions of the weld which contain defects reflect or transmit the ultrasonic signal differently than portions of the weld without defects, the reflected ultrasonic response signal received by the EMAT sensor carries with it information concerning the presence of defects in the weld.

Prior to utilizing the defect classification system 150 to determine the presence of defects in a weld on a test sample and classifying the type and/or severity of the defect, the ANN of the defect classification system 150 must be trained with a sample data set. The sample data set may include a collection of ultrasonic response signals which have been experimentally determined to correspond to a specific type of defect in a weld and/or the severity of the defect. The sample data set may be compiled by first determining the presence and location of defects in welds on one or more test samples through ultrasonic inspection. For example, the presence and location of a defect may be determined utilizing steps 202, 204 and 206 of the methodology shown in FIG. 7, which is described in more detail herein.

Once the location of a defect is determined, the weld sample may be destructively analyzed to qualitatively determine the type of defect present in the weld at the defect location and/or to assign a defect severity classification to the defect. For example, the weld sample may be subjected to a "cut check" test in which the weld sample is sectioned at the defect location. The sections may then be polished and analyzed to determine the type of defect present (e.g., blow hole, short legs, short throat, lack of penetration, etc.) and to assign the defect severity classification based on a quantitative assessment of the defect, as described above. For example, the defect may be assigned a letter classification of A, B, C or <C where A is indicative of no defect, B is indicative of a defect which is within permissible tolerances, C is indicative of a defect conditionally within permissible tolerances, and <C is a defect which is outside of permissible tolerances.

After the type of defect has been identified and/or a severity classification has been assigned to the defect, the type and/or severity of the defect may be coded into a vector representative of the type and/or severity of the defect. For example, in one embodiment, a four component target vector $B_T$ having components $<b_{T1}\ b_{T2}\ b_{T3}\ b_{T4}>$ may be assigned to the defect where component $b_{T1}$ is indicative of a lack of penetration defect, component $b_{T2}$ is indicative of a short leg defect, component $b_{T3}$ is a blow hole defect and component $b_{T4}$ is indicative of a short throat defect. Each component of the vector may be either a zero or a one where a one indicates the presence of the specific type of defect and zero indicates the absence of the defect. Table 1, shown below, contains exemplary target vectors indicative of specific types of defects. It should be understood that the target defect vector may also be indicative of a combination of defects. For example, a lack of penetration and short leg defect occurring at the same location may be represented by a vector coded as <1100>.

TABLE 1

Defect Type and Representative Target Defect Vector $B_T$

| DEFECT TYPE | Lack of Penetration | Short Leg | Blow Hole | Short Throat |
|---|---|---|---|---|
| TARGET DEFECT VECTOR | <1000> | <0100> | <0010> | <0001> |

Alternatively, when only the severity classification of a defect is assigned, the defect severity classification may be coded to a vector with each defect severity classification assigned a numeric value such that severity classification "A" has a numeric value of one, severity classification "B" has a numeric value of two, severity classification "C" has a numeric value of three and severity classification "<C" has a numeric value of four, as shown in Table 2 below.

TABLE 2

Defect Severity Classification and Target Severity Vector

| DEFECT SEVERITY | A | B | C | <C |
|---|---|---|---|---|
| TARGET SEVERITY VECTOR | <1> | <2> | <3> | <4> |

In yet another embodiment, both the defect type and severity may be coded into a single target defect vector. For example, the conventions described above in Tables 1 and 2 may be combined to produce a five component target defect vector where the first four components are indicative of the defect type and the last component is indicative of the defect severity classification. Accordingly, a target defect vector $B_T$ having a value <10004> may be indicative of a lack of penetration defect with a severity classification of <C.

Once the type and/or severity of the defect have been identified and coded in a target defect vector, the collected ultrasonic response signal corresponding to the defect location may be input into the ANN along with the ultrasonic response signals for measurement locations neighboring the defect location, as described below. In one embodiment, prior to inputting the signals into the ANN, the ultrasonic response signals may be pre-processed to reduce the overall number of data points in the ultrasonic response signals, as described herein. Utilizing the initialized weight matrices $V_{np}$ and $W_{pq}$ and the activation function for each neuron, the ANN outputs a vector B, as described above. However, for a given sample input entered into the ANN, the output vector B from the output layer $N_Z$ may not be equal to the target vector $B_T$ indicating that the values of the weight matrices $V_{np}$ and $W_{pq}$ need to be adjusted or trained.

A variety of neural network training algorithms may be used to adjust the weight matrices $V_{np}$ and $W_{pq}$ such that the ANN produces an output vector B corresponding to the target vector B of the sample data entered into the ANN. However, in the embodiments described herein, the ANN is trained with a back propagation algorithm. In the embodiment as depicted in FIG. 4, the back propagation algorithm, which may be performed by the controller, includes determining an output error or cost function E across the output layer $N_Z$ of the ANN. The error function may be written as:

$$E = \frac{1}{2}\sum_{m=1}^{q}(b_{Tm} - b_m)^2, \quad (1)$$

where $b_{Tm}$ is the target value for component m of the target vector $B_T$ and $b_m$ is the value of the corresponding output neuron $Z_m$. The variable m is an integer corresponding to the dimension q of the output vector B which is five in the exemplary neural networks shown and described herein. The value $b_m$ of each neuron $Z_m$ in output layer $N_Z$ may be calculated according to the equation:

$$b_m = \sum_{i=1}^{p} Y_i W_{im}, \quad (2)$$

where $Y_i$ is the value of a neuron in the preceding hidden layer and $W_{im}$ is the corresponding weight in weight matrix $W_{pq}$. The variable m may be an integer from 1 to q, as described above, while i is an integer from 1 to the total number of neurons in hidden layer $N_Y$, which in this example is p.

The value of $Y_i$ may be expressed as a function of the valued of the input layer neurons and the weight matrix $V_{np}$ such that:

$$Y_i = f\left(\sum_{l=1}^{n} a_l V_{li}\right), \quad (3)$$

where i is an integer as described above and l is an integer from 1 to the total number of input neurons n and $f$ is the activation function. Alternatively, the value for $Y_i$ may generally be expressed as function the activation function for each neuron in the hidden layer $N_Y$.

New or adjusted values for each weight in the weight matrices $V_{np}$ and $W_{pq}$ may be determined by using the cost function E for a given set of sample inputs. Specifically, the values for each component of matrices $V_{np}$ and $W_{pq}$ may be adjusted by moving along the cost function in a direction opposite the gradient to the minimum of the cost function (i.e., where the value of the cost function E yields the smallest amount of total error in the input/output mapping). For the weight matrix $W_{pq}$ between the hidden layer $N_Y$ and the output layer $N_Z$ this may be accomplished by taking the partial derivative of the cost function E with respect to a weight $W_{im}$ which may be expressed mathematically as:

$$\frac{\partial E}{\partial W_{im}} = \frac{\partial}{\partial W_{im}}\left[\frac{1}{2}\sum_{m=1}^{q}(b_{Tm} - b_m)^2\right] \quad (4)$$

$$= (b_{Tm} - b_m)Y_i. \quad (5)$$

The value of a particular weight $W_{im}$ in the weight matrix $W_{pq}$ may be adjusted by subtracting the partial derivative of the cost function with respect to $W_{im}$ such that $$W_{im}^{new} = W_{im}^{old} - \alpha \frac{\partial E}{\partial W_{im}}, \quad (6)$$

where α is a positive constant-valued learning rate which regulates the amount of adjustment made with each move or step along the gradient of the cost function E. Similarly, for the weight matrix $V_{np}$ between the input layer $N_X$ and the hidden layer $N_Y$, new values for each weight $V_{li}$ in the matrix may be mathematically determined from the cost function by taking the partial derivative of the cost function E with respect to a weight $V_{li}$ such that the new value for $V_{li}$ may be written as:

$$V_{li}^{new} = V_{li}^{old} - \beta \frac{\partial E}{\partial V_{li}}, \quad (7)$$

where β is a positive constant-valued learning rate which regulates the amount of adjustment made with each move along the gradient of the cost function E.

Equations 6 and 7 may be used to adjust each weight value in the weight matrices $V_{np}$ and $W_{pq}$ such that the output vector B of the ANN more closely approximates the values of the experimentally determined target vector $B_T$. The same algorithm may be used in conjunction with each test sample in the sample data set. The training process is iterated until the total sum of errors between the output vector B of the ANN and the target vector $B_T$ is within the a prescribed tolerance.

Figure 7:
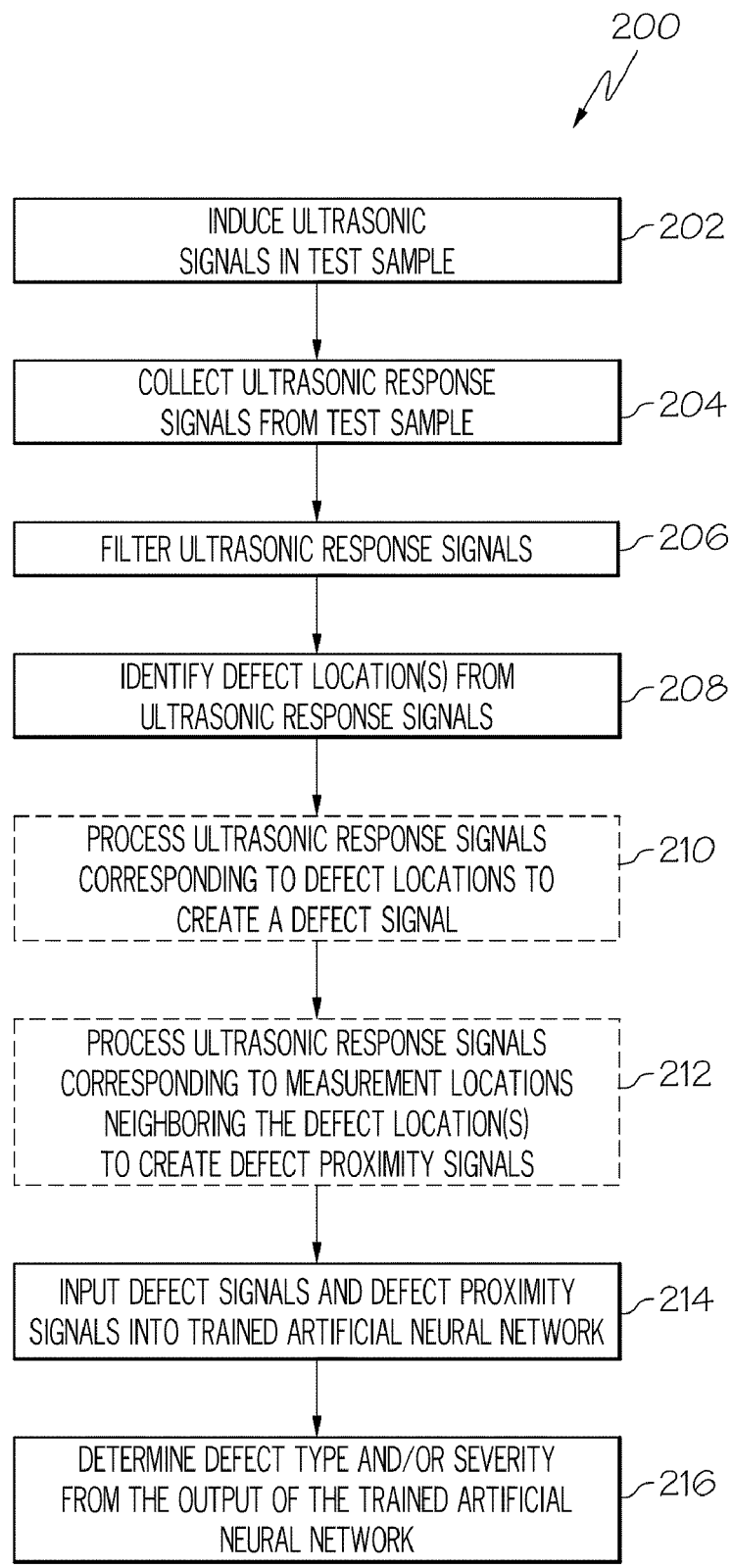
FIG. 7 is a flow diagram of a method for classifying the type and/or severity of a defect in a weld according to one or more embodiments shown and described herein.

Referring now to FIGS. 2 and 7, one embodiment of a method 200 for detecting the presence, type and/or severity of defects in a weld with the defect classification system 150 is depicted. In a first step 202, the controller triggers the pulsed laser source 105 to induce an ultrasonic signal in the test sample 110 by directing a series of beam pulses onto the surface of the test sample, as described above. The controller may be programmed to trigger the pulsed laser source multiple times at each measurement location and the collected ultrasonic response signals generated by each firing of the pulsed laser at each measurement location may be averaged to increase the signal to noise ratio of the collected ultrasonic response signal at that location. In the embodiments described herein the pulsed laser source is operated in an ablative mode to induce ultrasonic response signals in the test sample which have frequency content from about 200 kHz to about 15 MHz. However, it should be understood that the pulsed laser source may also be operated in a thermoplastic mode to generate ultrasonic signals in the test sample. The ultrasonic signal propagates through the test sample 110 and the weld 140 and portions of the ultrasonic signal may be reflected by defects in the weld 140 or other features in the test sample while other portions of the ultrasonic response signal may be transmitted through the weld 140. In this example, the ultrasonic response signal is the signal transmitted or reflected after portions of the ultrasonic signal are reflected and/or defracted by defects and/or other features in the test sample.

In a second step 204, the ultrasonic response signal induced in the test sample 110 is collected with the EMAT sensor 107. In the embodiments described herein, the EMAT sensor 107 is positioned to collect an ultrasonic response signal which is transmitted through the weld 140, as illustrated in FIG. 2 and described above. The EMAT sensor 107 converts the collected ultrasonic response signal to an electrical signal which has a voltage proportional to the amplitude of the ultrasonic response signal. Accordingly, in the embodiments described herein where the collected ultrasonic response signal has been transmitted through the weld 140, electrical signals produced by the EMAT sensor 107 with relatively large voltages correspond to ultrasonic response signals with relatively greater amplitudes while electrical signals with relatively low voltages correspond to ultrasonic response signals with relatively lower amplitudes. The relative magnitude of the ultrasonic response signal may be generally indicative of the absence or presence of defects and/or manufacturing features in the test sample with lower amplitudes indicative of the presence of a defect and/or manufacturing feature and higher amplitudes indicative of the absence of a defect and/or manufacturing feature.

The electrical signal produced by the EMAT sensor 107 is transmitted from the EMAT sensor 107 to the controller (not shown) where the electrical signal is stored in a memory associated with the controller. The amplitude (i.e., the voltage) of the electrical signal is stored in the memory as a function of time and indexed or correlated to a specific position along the weld 140 of the test sample 110. Accordingly, it should be understood that the amplitude of the ultrasonic signal may be a function of both time (t) and position (x) along the weld 140 and, as such, may be written as $f(x,t)$.

After the collected ultrasonic response signal is stored in memory for one measurement location along the weld 140, the position of the test sample 110 relative to the pulsed laser source 105 and EMAT sensor 107 may be adjusted such that ultrasonic sonic response signals may be induced and collected from the test sample 110 at a different measurement location along the weld 140. In the embodiment shown in FIG. 2, the position of the test sample 110 relative to the pulsed laser source 105 and EMAT sensor 107 may be adjusted by the controller which sends a control signal to the stepper motor (not shown) coupled to the lead screw 122. Rotation of the stepper motor causes the lead screw 122 to rotate, which, in turn, imparts translational motion to the sample stage 108 thereby adjusting the position of the test sample 110 relative to the pulsed laser source 105 and EMAT sensor 107.

After the position of the test sample 110 has been adjusted, steps 202 and 204 may be repeated at a new location along the weld 140 and the amplitude of the ultrasonic response signal is stored in the memory operatively associated with the controller as a function of both time (t) and location (x) along the weld. This process of inducing an ultrasonic signal, collecting an ultrasonic response signal and adjusting the position of the test sample may be repeated multiple times to develop a set of ultrasonic response signals for a segment of the weld and/or the entire length of the weld 140.

Figure 9:
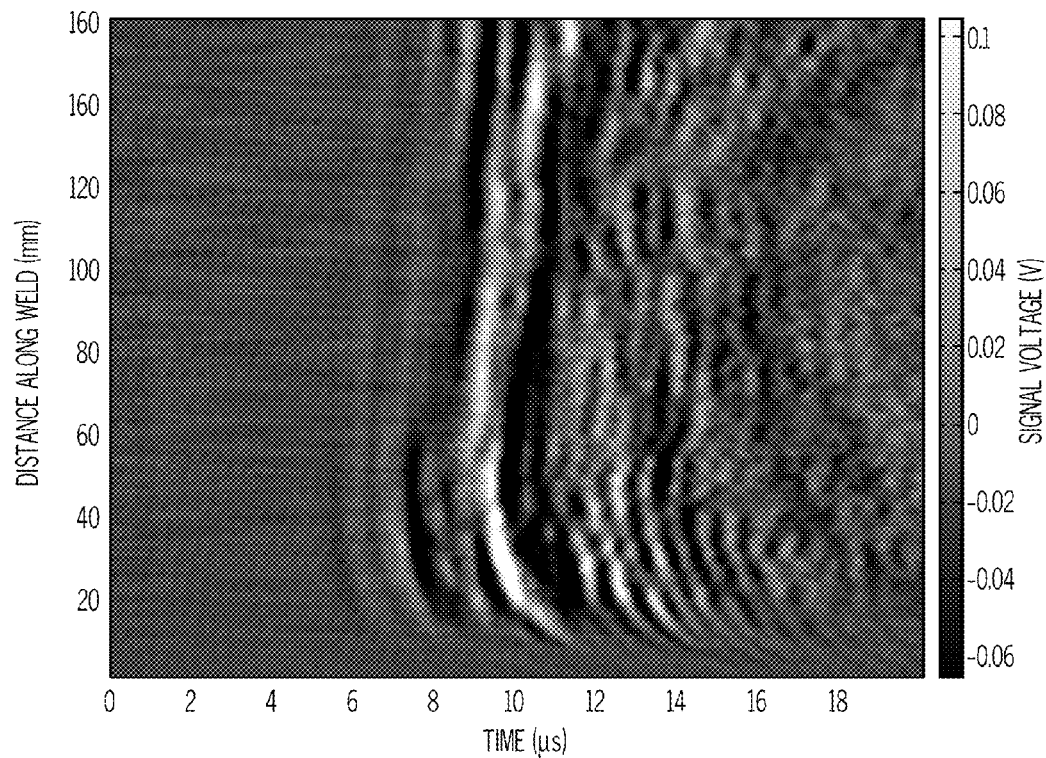
FIG. 9 is a plot of an ultrasonic response signal collected from a test sample according to one or more embodiments shown and described herein.

Referring now to FIG. 9, a set of ultrasonic response signals collected from one test sample are graphically illustrated. The y-axis is indicative of the position along the weld, the x-axis is indicative of the time interval over which the ultrasonic response signal was collected, and the gray scale is indicative of the relative amplitude of the collected ultrasonic response signal in units of voltage. The position of the test sample was adjusted in millimeter increments although larger or smaller increments may be used depending on the desired defect resolution.

Still referring to FIG. 9, the higher frequency/shorter wavelength content of the ultrasonic signals induced in the test sample may be more susceptible to diffraction and/or reflection by features in the test sample than other, lower frequencies. These features may include regular features (i.e., features regularly occurring in each of a plurality test samples) such as manufacturing features (e.g., connector holes, stamp marks, etc.) and irregular features such as defects. For example, one frequency range particularly susceptible to reflection and/or diffraction by these features may be from about 0.977 MHz to about 1.464 MHz. Accordingly, the corresponding frequencies in the ultrasonic response signal collected from the test sample may contain information regarding the presence of such features.

In one embodiment, at step 206, the controller may be programmed to filter the ultrasonic response signals collected from the test sample to isolate frequencies most susceptible to reflection and/or diffraction by features such as manufacturing features and/or defects. In the embodiments described herein, the collected ultrasonic response signals for each measurement location (x) along the weld may be filtered into frequency ranges that are sensitive to features (such as defects) in the test sample by first decomposing the collected ultrasonic response signal by discrete wavelet transform (DWT). Specifically, for a specified location x along the weld, the collected ultrasonic response signal $f(t)$ may be decomposed into a set of wavelet coefficients WS(h,k) according to the relationship:

$$WS(h,k) = \int f(t)\Psi_{h,k}^*(t)dt \tag{8}$$

where $\Psi^*_{h,k}(t)$ is the complex conjugate of wavelet $\Psi_{h,k}(t)$. Wavelet $\Psi_{h,k}(t)$ may be a function of a mother wavelet function $\Psi$ which is scaled by scaling parameter $s_0^h$ and shifted by shifting parameter $k\tau_0 s_0^h$ such that:

$$\Psi_{h,k}(t) = \frac{1}{\sqrt{s_0^h}} \Psi\left(\frac{t - k\tau_0 s_0^h}{s_0^h}\right), \tag{9}$$

where t is time and h and k are integers. $s_0$ is generally selected to be 2 and the shifting parameter $\tau_0$ is generally selected to be 1.

The selection of the mother wavelet $\Psi$ may depend on the shape or form of the collected ultrasonic response signal as a given ultrasonic response signal may be better approximated by a wavelet having a shape or form similar to that of the signal. The mother wavelet $\Psi$ used for decomposition of the ultrasonic response signal may be selected from, for example, the Daubechies wavelet family, the Coiflet wavelet family, the Haar wavelet family, the Symmlet wavelet family, the Discrete Meyer (DMEY) wavelet or similar wavelet families. For example, in one embodiment wavelet 6 of the Daubechies wavelet family may be used as the mother wavelet $\Psi$ to decompose the ultrasonic response signal. However, it should be understood that other mother wavelets may be used.

As shown above, decomposition of the ultrasonic response signal for each measurement location x by DWT produces a set of wavelet coefficients WS(h,k) for that measurement location. After decomposition, the controller may be programmed to band-pass filter each resulting set of wavelet coefficients to isolate a frequency range most sensitive to defects which, in the embodiments described herein, is from about 0.977 MHz to about 1.464 MHz. Filtering the set of wavelet coefficients is performed by zeroing elements of the wavelet coefficient WS(h,k) that correspond to frequency content outside the desired frequency range. In the embodiments described herein, decomposition by DWT and filtering may be performed by the controller using Mallet's filter banks algorithm which produces a band-pass filtered set of wavelet coefficients for each measurement location along the weld.

After each collected ultrasonic response signal is decomposed by DWT and the resulting wavelet coefficients are filtered to isolate the desired frequency content, the controller may be programmed to reconstruct a filtered response signal $f(x,t)$ for each measurement location from the corresponding filtered sets of wavelet coefficients by inverse discrete wavelet transform (IDWT) to form a filtered response signal for each measurement location x along the weld. For example, when there are 120 separate measurement locations along the weld, 120 filtered response signals are created by IDWT.

Referring again to FIG. 7, in step 208, the controller may be programmed to identify the presence and location of defects in the weld and store the location and ultrasonic response signal corresponding to any identified defects in memory for use in classifying the type and/or severity of the defects. The ultrasonic response signal for measurement locations neighboring the defect location may also be stored in memory for use in classifying the type and/or severity of the defect. The controller may be programmed to identify the presence and location of defects in the weld by analyzing the ultrasonic response signals collected from each measurement location along the weld. For example, in one embodiment, the controller may be programmed to identify the location of defects in a weld using the methodologies disclosed in co-pending U.S. patent application Ser. No. 12/488,396 entitled "METHODS AND SYSTEMS FOR DETECTING DEFECTS IN WELDED STRUCTURES", which is herein incorporated by reference. In another embodiment, which is described more fully herein, the controller may be programmed to identify the location of defects in the weld by monitoring fluctuations in the energy of the ultrasonic response signal and/or comparing fluctuations in the energy of the ultrasonic response signal to known energy defect patterns.

Figure 8:
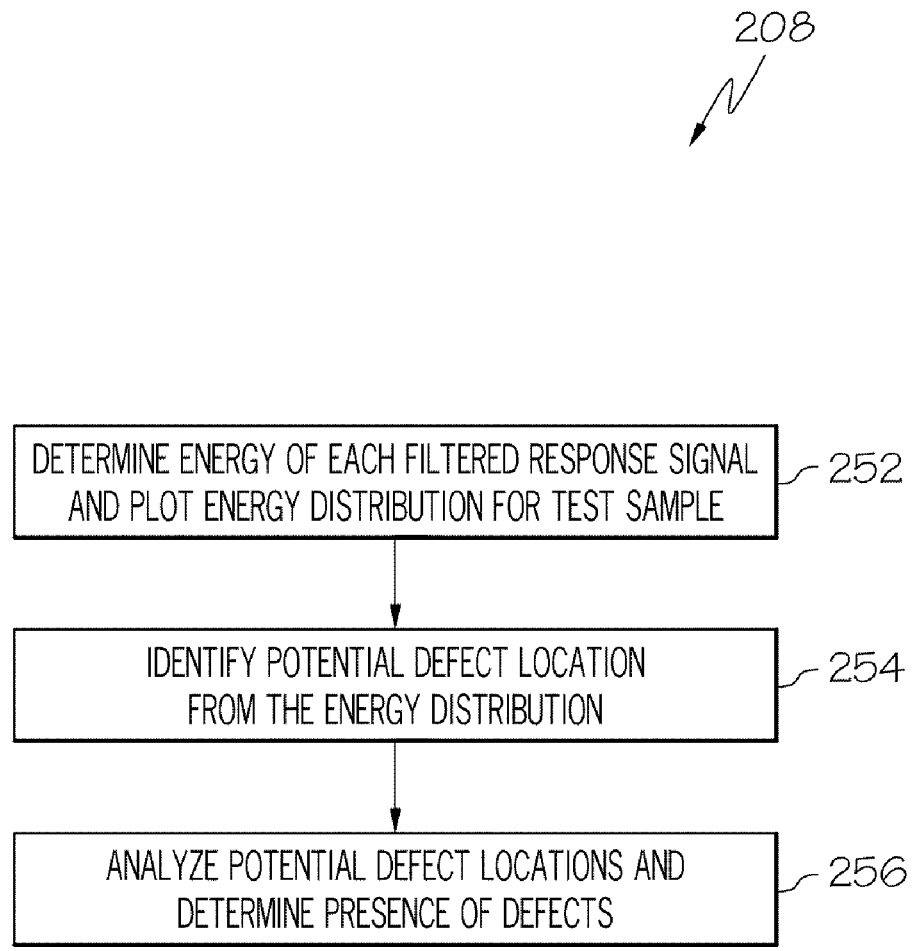
FIG. 8 is flow diagram of a method for determining the presence of a defect in a welded structure according to one or more embodiments shown and described herein.

Referring now to FIG. 8, a flow diagram of one embodiment of a method for performing step 208 is depicted. In this embodiment, the presence of defects in the weld is determined by monitoring fluctuations in the energy of the ultrasonic response signal and/or comparing fluctuations in the energy of the ultrasonic response signal to known energy defect patterns. In step 252 the controller may be programmed to calculate and normalize an energy $E(x)$ for each measurement location x on the test sample based on the corresponding filtered response signals $f(x,t)$ for the measurement location. The energy $E(x)$ for each measurement location x may be calculated by summing the square of the corresponding filtered response signal $f(x,t)$ over the time duration of the signal such that:

$$E(x) = \sum_t (f(x,t))^2, \quad (10)$$

where $E(x)$ is the energy at location x and $f(x,t)$ is the amplitude of the filtered ultrasonic response signal at location x and time t.

Figure 10:
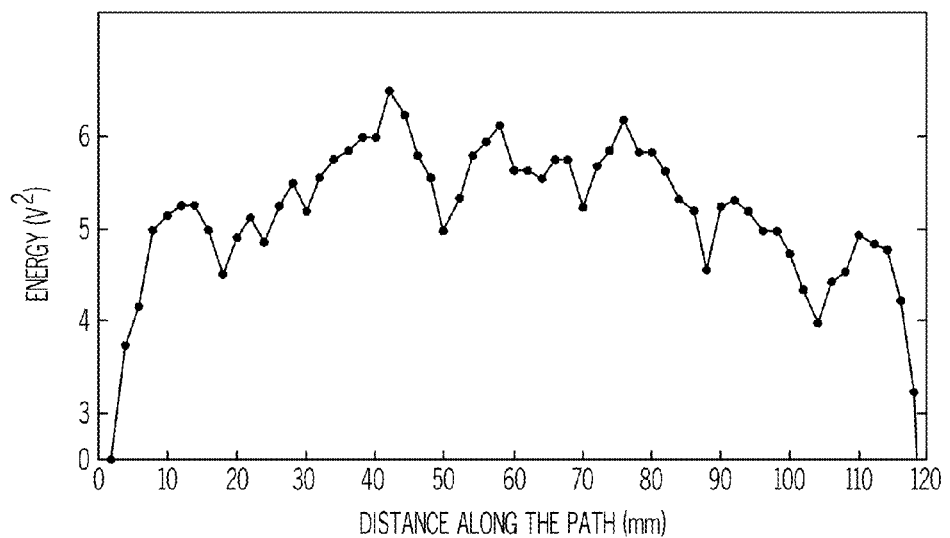
FIG. 10 is a plot of an energy distribution derived from the ultrasonic response signal of FIG. 9.

Based on the energy $E(x)$ for each measurement location along the weld, an energy distribution may be plotted as depicted in FIG. 10 where the x-axis corresponds to the measurement location x along the weld and the y-axis corresponds to the ultrasonic signal energy $E(x)$ for each measurement location. The plotted energy distribution shows that the energy of the ultrasonic response signal fluctuates along the length of the weld. These fluctuations in energy may be caused by the presence of various features in the test sample and/or weld which may reflect or diffract the ultrasonic signal induced in the test sample. Such features may include regular features, such as stamp marks, connector holes, and the like, or irregular features, such as defects and/or changes in the thickness of the weld, as described above.

Figure 12:
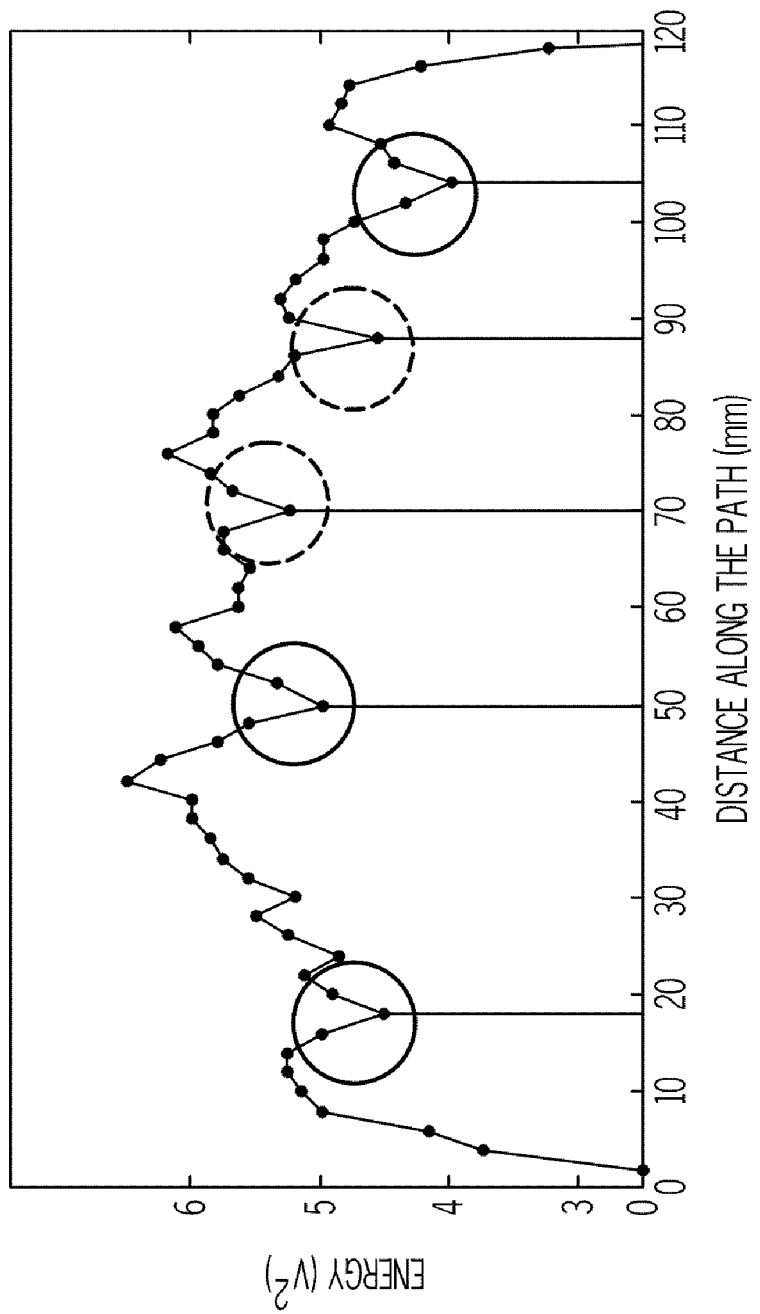
FIG. 12 is a plot of the energy distribution of FIG. 10 with potential defect locations identified.

Referring now to FIGS. 8, 10 and 12, in a next step 254, the controller may be programmed to identify potential defect locations along the weld utilizing the energy $E(x)$ for each measurement location and/or a plotted energy distribution, such as the plotted energy distribution shown in FIG. 10. To identify potential defect locations, the controller may compare the energy $E(x)$ for each measurement location x to the energy of adjacent measurement locations, such as, for example, measurement locations x−1 and x+1. If the energy $E(x)$ is a local minimum (e.g., $E(x-1)>E(x)$ and $E(x+1)>E(x)$) then measurement location x is a potential defect location. Examples of potential defect locations are indicated by the circled points in the plotted energy distribution shown in FIG. 12. Where $E(x)$ is a local minimum, the controller may designate the position x of the local minimum as a potential defect location $x_{pd}$ and stores the potential defect location $x_{pd}$ in a memory operably associated with the controller.

Referring now to FIGS. 8 and 10-12, in a next step 256, the controller may be programmed to analyze fluctuations in the ultrasonic energy at measurement locations neighboring each potential defect location $x_{pd}$ to determine the presence of defects in the weld utilizing the energy $E(x_{pd})$ of the potential defect location $x_{pd}$ and the energy of neighboring measurement locations. In one embodiment, the controller may analyze each potential defect location $x_{pd}$ for the presence of defects by comparing the energy $E(x_{pd})$ of the potential defect location and the energy of adjacent measurement locations to a set of defect energy patterns, such as the exemplary defect energy patterns graphically depicted in FIGS. 11A-11J, which may be stored in the memory operatively associated with the controller.

The defect energy patterns shown in FIGS. 11A-11J may be derived from test samples which have been destructively examined after ultrasonic signals have been induced in the test samples and ultrasonic response signals have been collected from the test samples, as described above. An energy distribution for each test sample may then be plotted and the results of the destructive examination of each test sample may be compared to the corresponding energy distribution to correlate fluctuations in the energy distribution to the defects identified through destructive examination. Based on these comparisons a set of defect energy patterns may be identified which correspond to fluctuations in the energy distribution caused by defects.

In order to determine if a potential defect location $x_{pd}$ contains an actual defect, the controller compares the pattern formed by the energy $E(x_{pd})$ of each potential defect location $x_{pd}$ and the energy of neighboring measurement locations on each side of the potential defect location $x_{pd}$ to the defect energy patterns and, if the patterns have a similar shape, the controller designates the potential defect location $x_{pd}$ as a defect location $x_D$ and stores this location as a defect location in the memory operatively associated with the controller.

Referring to FIGS. 11 and 12 by way of example, a potential defect location $x_{pd}$ is present at x=104 mm. The pattern formed by the energy $E(x_{pd})$ of this potential defect location and the energy of measurement locations on each side of the potential defect location (e.g., the 3 measurement locations to the left of x=104 mm and the three measurement locations to the right of x=104 mm) form a pattern similar to the defect energy pattern of FIG. 11I and, as such, the controller identifies the potential defect location at x=104 mm as a defect location $x_D$ and stores this location in memory as a defect.

In an alternative embodiment, at step 256, the controller may be programmed to analyze each potential defect location $x_{pd}$ by comparing the energy $E(x)$ at each potential defect location $x_{pd}$ to the energy of a plurality of neighboring measurement locations. The controller may compare the energy for potential defect location $x_{pd}$ to the energy for at least two consecutive measurement locations on each side of the potential defect location $x_{pd}$. For example, the controller may compare the energy for points $x_{pd}$-1, $x_{pd}$-2 ... $x_{pd}$-i on one side of $x_{pd}$, and to points $x_{pd}$+1, $x_{pd}$+2 ... $x_{pd}$+j on the other side of $x_{pd}$, where i and j are integers, i<$x_{pd}$ and 1≦j≦n-$x_{pd}$ and n is the total number of measurement locations along the weld.

If the ultrasonic energy on each side of the potential defect location increases monotonically for each of the neighboring measurement locations, and if the number of neighboring measurement locations with monotonically increasing energy is between two and four on each side of the defect location, then the controller identifies the potential defect location $x_{pd}$ as a defect location $x_D$ and stores the location in a memory operatively associated with the controller. As shown in FIG. 12, locations enclosed by a solid circle (e.g., at x=18 mm, 50 mm and 104 mm) are indicative of defect locations and the locations enclosed by a dashed circle (e.g., at x=70 mm and 88 mm) are potential defect locations which, after further analysis by the controller, do not meet the criteria for the presence of a defect (i.e., the ultrasonic energy does not increase monotonically over at least two neighboring measurement locations or it increases monotonically over more than four neighboring measurement locations on each side of the potential defect location).

Figure 11A:
FIGS. 11A-11J schematically depict defect energy patterns which may be used to identify the presence of defects in a weld by comparison to an energy distribution, such as the energy distribution of FIG. 10, according to one or more embodiments shown and described herein.
Figure 11B:
Figure 11C:
Figure 11D:
Figure 11E:
Figure 11F:
Figure 11G:
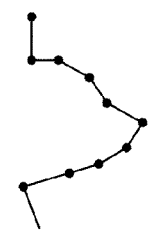
Figure 11H:
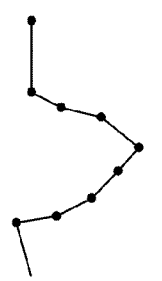
Figure 11I:
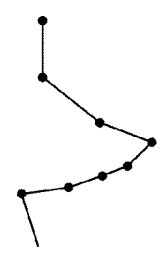
Figure 11J:
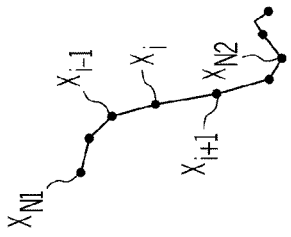

In one embodiment, after the ultrasonic energy of the potential defect location is compared to at least two neighboring defect locations on each side of the potential defect location to determine if the ultrasonic energy increases monotonically, the energy of the potential defect location and the energy of neighboring measurement locations may be compared to defect energy patterns stored in memory, as described above, to further assess whether the potential defect location contains a particular defect, such as, for example, a lack of penetration defect which has a defect energy pattern as shown in FIG. 11J. If the ultrasonic energy at the potential defect location and the ultrasonic energy at the neighboring defect locations corresponds to a defect energy pattern, then the controller designates the potential defect location $x_{pd}$ as a defect location $x_D$ and stores the location in memory as a defect.

In another embodiment, in order to identify a lack of penetration defect such as that shown in FIG. 11J, the controller may be programmed to first identify local maximum and minimum pairs by comparing the energy of each measurement location to the energy of neighboring measurement locations. For example, the points $X_{N1}$ and $X_{N2}$ shown in FIG. 11J are indicative of local maximum and minimum, respectively. Thereafter, the average slope between the local maximum and minimum may be determined utilizing the following equation:

$$slope_{avg} = \frac{E(X_{N2}) - E(X_{N1})}{X_{N2} - X_{N1}}, \quad (11)$$

where $E(X_{N2})$ is the energy at measurement location $X_{N2}$ and $E(X_{N1})$ is the energy at measurement location $X_{N1}$.

Thereafter, for each point $X_i$ between $X_{N1}$ and $X_{N2}$, the controller may be programmed to determine the slope between points $X_i$ and $X_{i-1}$ and the slope between points $X_i$ and $X_{i-1}$ and compare each slope to the averaged slope. If the absolute value of the slope between points points $X_i$ and $X_{i-1}$ and the absolute value of the slope between points $X_i$ and $X_{i+1}$ are both greater than the average slope, then the point $X_i$ is a defect location.

In yet another embodiment, at step 256, the controller may be programmed to analyze each potential defect location $x_{pd}$ by comparing the energy E(x) at each potential defect location $x_{pd}$ to the energy of a plurality of neighboring measurement locations, as described above. When the energy on each side of the potential defect location increases monotonically for each of the neighboring measurement locations, the controller identifies the potential defect location $x_{pd}$ as a defect location $x_D$ and stores the location in a memory operatively associated with the controller.

Referring now to FIGS. 3 and 9, in one embodiment, after a defect location has been identified, the controller may optionally process ultrasonic response the signals corresponding to the defect location and measurement locations on either side of the defect location with signal processing module 302 prior to inputting the signals to the ANN 304. The signal processing module may be either integral with the controller or a separate unit electrically coupled to the controller. Accordingly, the method 200 may proceed to step 210 where the ultrasonic signal corresponding to the identified defect location may be processed. In step 210 the ultrasonic signal corresponding to the defect location (hereinafter referred to as the defect signal) may be processed to reduce the overall number of data points in the defect signal. For example, in one embodiment, the defect signal may be divided into a plurality of segments or windows based on time. The number of segments used may vary depending on the total number of data points in the defect signal. In the embodiments described herein, 200 segments were used. After the defect signal is segmented, an average of each segment may then be calculated and the defect signal reconstructed using the average of each segment. Accordingly, it should be understood that, after processing, the defect signal comprises a total number of points equal to the number of segments used which, in the embodiments described herein, is 200.

In a next step 212, the controller may optionally process the ultrasonic response signals corresponding to measurement locations neighboring the defect location (hereinafter the defect proximity signals) in a similar manner as the defect signals to reduce the total number of points in each defect proximity signal. As described herein, the defect proximity signals are the ultrasonic signals for measurement locations neighboring the defect location which may be effected by the presence of the defect and, as such, may be useful in classifying the type and/or severity of the defect. In the embodiments described herein, a total often defect proximity signals are utilized (five on either side of the defect location). However, it should be understood that more or fewer defect proximity signals may be utilized to determine the type and severity of the defect in the weld. After the defect proximity signals are processed, each defect proximity signal may comprise a total number of points equal to the number of segments used in processing which, in the embodiments described herein is 200.

Referring now to FIGS. 3, 4 and 7, in a next step 214, the controller may input the defect signal and the defect proximity signals into the input layer of the previously trained ANN 304. In the embodiments described herein, the controller may input the defect signal and the defect proximity signals into the ANN 304 by first creating an input vector A which comprises the defect signal and defect proximity signals. The input vector A generally has a dimension of n where n is an integer representing the number of components in the vector (i.e., $a_1, a_2, a_3, \ldots a_n$). In the examples described herein, there is one defect signal and ten defect proximity signals such that the input vector A comprises a total of 11 signals. If each signal is processed as described above, each signal will have a total of 200 points, with each point corresponding to a component in the vector. Accordingly, for eleven signals each having 200 points, the input vector A has a dimension n of 11×200 such that n=2200.

While in the aforementioned example the dimension n of the input vector A is 2200, it should be understood that input vectors of larger or smaller dimensions may be used. For example, where fewer defect proximity signals are used, the dimension of the input vector A may be smaller. However, where more segments are used in processing the signal, the dimension of the input vector may be larger. Moreover, when the defect signal and the defect proximity signals are not processed to reduce the number of data points in each signal, the dimension n of the input vector A may be significantly larger depending on the number of data points in each of the defect signal and defect proximity signals.

After the controller creates the input vector A from the defect signal and the defect proximity signals, the controller passes the input vector A to the input layer $N_X$ of the ANN 304. As described above and shown in FIG. 4, the input layer $N_X$ of the ANN 304 comprises n input nodes. Accordingly, each component of the input vector A is passed to a separate input node of the ANN 304. Utilizing the weight matrices determined during training of the ANN 304 and the activation function associated with each node of each layer, the ANN 304 performs a series of mathematical operations on the input vector A and outputs a coded defect vector B which relates to the identity and/or severity classification of the defect corresponding to the defect signal. In the embodiments described herein, the defect vector B is coded to identify one of four different types of defects and/or combinations thereof. The defect vector also contains the severity classification of the identified defect, as described above. Accordingly, the defect vector B has a dimension of 5 (i.e., q=5).

For example, using the conventions described hereinabove for the defect vector B, when the trained ANN 304 determines that the input vector A is indicative of a short leg defect having a defect severity classification of B, the ANN 304 outputs a defect vector of <01002> where the 1 at positions b1 is indicative of a short leg defect and the 2 at position b5 is indicative of a defect severity classification of "B".

As described hereinabove, the dimension of the output layer $N_Z$ of the ANN 304 (and therefore the dimensions of defect vector B) may be reduced or expanded to identify a different number of defect types and/or combinations of defect types. Further, additional severity classifications or severity sub-classifications may be added to the output layer $N_Z$ to provide additional information on the severity of the defect.

Further, while the defect vector B is described herein as comprising both an identification of the defect and the severity classification of the defect, it should be understood that, in other embodiments, the defect vector B may include either the defect identification or the defect severity classification.

In a next step 216, the controller may be programmed to decode the defect vector B and output the defect type and/or severity classification indicated by the defect Vector B. For example, the controller may provide a visual and/or audible indication of the presence of defects in the weld as well as an indication of the type of defect and/or the severity of the defect. In one embodiment, where the defect classification system 150 comprises a display, the controller may be programmed to plot an energy distribution on the display similar to that shown in FIG. 12. The controller may also be programmed to identify defect locations on the display and identify the type and/or severity of each defect at each defect location. For example, where the controller is programmed to display a plot of the energy distribution on the display, the controller may be programmed to graphically indicate the location $x_D$ of defects on the energy distribution and provide a corresponding indication of the type and/or severity of each defect located. Alternatively or additionally, the controller may be programmed to display the location of each defect. For example, referring to the plot of the energy distribution shown in FIG. 12, the controller may be operable to indicate on the display that a blowhole defect of severity "B" is located at x=18 mm, a lack of penetration depth defect of severity "C" is located at x=50 mm and a combined lack of penetration/short leg defect of severity "<C" is located at x=104 mm.

It should now be understood that the defect classification system and methods shown and described herein may be used to classify the type and/or severity of defects present in a weld utilizing ultrasonic signals. The system may be implemented in a manufacturing environment to perform automated inspection of welded structures of various configurations. The system may be used as a quality control tool for each welded structure produced or, alternatively, to analyze a random sampling of the welded structures produced.

While the defect classification systems described herein utilize non-contact methods for inducing an ultrasonic signal in the test sample and collecting an ultrasonic response signal from the test sample, it should be understood that the methods utilized by the defect classification systems may also be used by ultrasonic inspection systems which utilize acoustic signal generators and/or acoustic signal detectors which physically contact the test sample.

Further, while the methods for classifying the type and/or severity of a defect in a weld are described herein as being performed in conjunction with inducing an ultrasonic signal in the test sample and collecting ultrasonic response signals from the test sample, it should be understood that the method for classifying the type and/or severity of a defect in a weld may be performed independently from the steps of inducing an ultrasonic signal and collecting an ultrasonic response signal. For example, the collected ultrasonic response signals may be stored in the controller and analyzed according to the methods described herein at a later time.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for determining a type of a defect in a weld comprising:
    determining a defect location and a defect signal corresponding to the defect location by analyzing ultrasonic response signals collected from a plurality of measurement locations along the weld;
    inputting the defect signal and a plurality of defect proximity signals into a trained artificial neural network, wherein the plurality of defect proximity signals correspond to ultrasonic response signals from measurement locations on each side of the defect location and the trained artificial neural network is operable to:
- identify the type of the defect located at the defect location based on the defect signal and the plurality of defect proximity signals; and
- output the type of the defect located at the defect location.

2. The method of claim 1 further comprising processing the defect signal and the plurality of defect proximity signals prior to inputting the defect signal and the plurality of defect proximity signals into the trained artificial neural network.

3. The method of claim 2 wherein the defect signal and the plurality of defect proximity signals are processed by dividing each signal into a plurality of segments and averaging each segment.

4. The method of claim 1 wherein the trained artificial neural network is operable to identify the type of the defect as a blow hole defect, a lack of penetration defect, a short leg defect, a lack of penetration/short leg defect or combinations thereof.

5. The method of claim 1 wherein the trained artificial neural network is further operable to:
- determine a severity classification of the defect located at the defect location based on the defect signal and the plurality of defect proximity signals; and
- output the severity classification of the defect located at the defect location.

6. The method of claim 5 wherein the trained artificial neural network outputs a coded vector indicative of the type and severity classification of the defect.

7. The method of claim 1 wherein the trained artificial neural network is trained with a back propagation algorithm using a sample data set derived from destructively tested weld samples.

8. The method of claim 1 wherein the defect location is determined by:
- filtering an ultrasonic response signal from each of the measurement locations to produce a filtered response signal for each of the measurement locations;
- calculating an ultrasonic energy for each of the measurement locations with the filtered response signal corresponding to each of the measurement locations;
- comparing the ultrasonic energy for each measurement location to the ultrasonic energy of adjacent measurement locations to identify potential defect locations, wherein, when the ultrasonic energy of a measurement location is less than the ultrasonic energy of the adjacent measurement locations, the measurement location is a potential defect location; and
- analyzing fluctuations in the ultrasonic energy at measurement locations neighboring the potential defect locations to determine if a defect is present in the weld.

9. A method for determining a severity of a defect in a weld comprising:
- determining a defect location and a defect signal corresponding to the defect location by analyzing ultrasonic response signals from a plurality of measurement locations along the weld;
- inputting the defect signal and a plurality of defect proximity signals into a trained artificial neural network, wherein the plurality of defect proximity signals correspond to ultrasonic response signals from measurement locations on each side of the defect location and the trained artificial neural network is operable to:
  - determine a severity classification of the defect located at the defect location based on the defect signal and the plurality of defect proximity signals; and
  - output the severity classification of the defect located at the defect location.

10. The method of claim 9 further comprising processing the defect signal and the plurality of defect proximity signals prior to inputting the defect signal and the plurality of defect proximity signals into the trained artificial neural network.

11. The method of claim 10 wherein the defect signal and the plurality of defect proximity signals are processed by dividing each of the signals into a plurality of segments and averaging each segment.

12. The method of claim 9 wherein the trained artificial neural network is trained with a back propagation algorithm using a sample data set derived from destructively tested weld samples.

13. The method of claim 9 wherein the defect location is determined by:
- filtering an ultrasonic response signal from each of the measurement locations to produce a filtered response signal for each of the measurement locations;
- calculating an ultrasonic energy for each of the measurement locations with the filtered response signal corresponding to each of the measurement locations;
- comparing the ultrasonic energy for each of the measurement locations to the ultrasonic energy of adjacent measurement locations to identify potential defect locations, wherein, when the ultrasonic energy of a measurement location is less than the ultrasonic energy of the adjacent measurement locations, the measurement location is a potential defect location; and
- analyzing fluctuations in the ultrasonic energy at measurement locations neighboring the potential defect locations to determine if a defect is present in the weld.

14. A defect classification system for identifying a type of a defect in a weld, the defect classification system comprising a controller, an acoustic signal generator, an acoustic signal detector, and a positioning device, wherein the acoustic signal generator, the acoustic signal detector and the positioning device are electrically coupled to the controller and the controller is programmed to:
- induce ultrasonic signals at multiple measurement locations along the weld with the acoustic signal generator;
- collect an ultrasonic response signal from each of the measurement locations with the acoustic signal detector and store each ultrasonic response signal in a memory operatively associated with the controller;
- determine a defect location and a defect signal by analyzing the ultrasonic response signal from each of the measurement locations;
- determine a plurality of defect proximity signals, wherein the plurality of defect proximity signals correspond to ultrasonic response signals from measurement locations on each side of the defect location;
- input the defect signal and the plurality of defect proximity signals into a trained artificial neural network operatively associated with the controller, wherein the trained artificial neural network is operable to identify the type of the defect located at the defect location based on the defect signal and the plurality of defect proximity signals; and
- output the type of the defect located at the defect location.

15. The defect classification system of claim 14 wherein the trained artificial neural network outputs a coded vector indicative of the type of the defect.

16. The defect classification system of claim 14 wherein the trained artificial neural network is further operable to:
   determine a severity classification of the defect located at the defect location based on the defect signal and the plurality of defect proximity signals; and
   output the severity classification of the defect located at the defect location.

17. The defect classification system of claim 16 wherein the trained artificial neural network outputs a coded vector indicative of the type and severity classification of the defect.

18. The defect classification system of claim 14 wherein the controller is further programmed to process the defect signal and the plurality of defect proximity signals prior to inputting the defect signal and the plurality of defect proximity signals into the trained artificial neural network.

19. The defect classification system of claim 18 wherein the controller is programmed to process the defect signal and the plurality of defect proximity signals by dividing each signal into a plurality of segments and averaging each segment.

20. The defect classification system of claim 14 wherein the trained artificial neural network is trained with a back propagation algorithm using a data set derived from destructively tested weld samples.

* * * * *